(12) United States Patent
Weinstein (10) Patent No.: US 11,318,042 B2
(45) Date of Patent: May 3, 2022

(54) THERMAL PACK THAT CONFORMS TO CURVED SURFACES

(71) Applicant: Randy H Weinstein, Windsor, CA (US)

(72) Inventor: Randy H Weinstein, Windsor, CA (US)

( * ) Notice: Subject to any disclaimer, the term of this patent is extended or adjusted under 35 U.S.C. 154(b) by 0 days.

(21) Appl. No.: 15/553,988

(22) PCT Filed: Mar. 29, 2017

(86) PCT No.: PCT/US2017/024871
§ 371 (c)(1),
(2) Date: Sep. 21, 2017

(87) PCT Pub. No.: WO2018/063441
PCT Pub. Date: Apr. 5, 2018

(65) Prior Publication Data
US 2019/0216640 A1    Jul. 18, 2019

Related U.S. Application Data

(63) Continuation of application No. 15/280,988, filed on Sep. 29, 2016.

(51) Int. Cl.
*A61F 7/10* (2006.01)
*A61F 7/02* (2006.01)
(Continued)

(52) U.S. Cl.
CPC ............. *A61F 7/10* (2013.01); *A61F 7/02* (2013.01); *B65D 81/18* (2013.01); *B65D 81/382* (2013.01);
(Continued)

(58) Field of Classification Search
CPC ............. A61F 7/10; A61F 2007/0268; A61F 2007/0273
See application file for complete search history.

(56) References Cited

U.S. PATENT DOCUMENTS 2,337,550 A    12/1943    Crosby .................. 264/250
3,830,676 A    8/1974    Elkins
(Continued)

FOREIGN PATENT DOCUMENTS

CN    106166097    11/2016
EP    2208484    7/2010    ............. A61F 7/10
(Continued)

OTHER PUBLICATIONS

International Search Report and Written Opinion issued in corresponding foreign application, PCT/US2017/024871, pp. 1-6 (dated May 22, 2017).
(Continued)

*Primary Examiner* — Kaitlyn E Smith
*Assistant Examiner* — Sean W Collins
(74) *Attorney, Agent, or Firm* — Benjamin D. Rotman; Golan Christie Taglia LLP (57) ABSTRACT

The present disclosure is for a therapeutic thermal pack configured to conform to three dimensional surfaces. The therapeutic thermal pack comprises first and second plastic sheets bound together forming a sack. The sack further comprises a plurality of joint lines forming open or closed cells within the boundary of the sack. The open and closed cells are configured to enhance the flexibility of the sack. The sack contains a flowable thermal material within the open or closed cells.

19 Claims, 8 Drawing Sheets

(51) Int. Cl.
　　　*B65D 81/18*　　　(2006.01)
　　　*B65D 81/38*　　　(2006.01)
　　　*A61F 7/00*　　　(2006.01)
(52) U.S. Cl.
　　　CPC ... *A61F 2007/003* (2013.01); *A61F 2007/004* (2013.01); *A61F 2007/0008* (2013.01); *A61F 2007/0014* (2013.01); *A61F 2007/0032* (2013.01); *A61F 2007/0035* (2013.01); *A61F 2007/0042* (2013.01); *A61F 2007/0045* (2013.01); *A61F 2007/0219* (2013.01); *A61F 2007/0228* (2013.01); *A61F 2007/0273* (2013.01); *A61F 2007/108* (2013.01)

(56) References Cited

U.S. PATENT DOCUMENTS

| | | | | |
|---|---|---|---|---|
| 4,753,241 A | * | 6/1988 | Brannigan | A61F 7/02 156/210 |
| 5,107,444 A | | 4/1992 | Wu | |
| 5,129,391 A | * | 7/1992 | Brodsky | A61F 7/10 607/110 |
| 5,230,335 A | | 7/1993 | Johnson, Jr. et al. | 128/400 |
| 5,423,875 A | * | 6/1995 | Kehe | A61F 7/10 607/112 |
| 5,496,357 A | | 3/1996 | Jensen et al. | |
| 5,634,940 A | | 6/1997 | Panyard | |
| 5,683,439 A | | 11/1997 | Jensen | |
| 9,439,803 B2 | | 9/2016 | Varga et al. | A61F 7/02 |
| 2003/0204227 A1 | * | 10/2003 | Ingram | A61F 7/02 607/114 |
| 2004/0064168 A1 | | 4/2004 | Eischen | |
| 2008/0009926 A1 | * | 1/2008 | Russak | A61F 7/02 607/109 |
| 2008/0288033 A1 | | 11/2008 | Mason et al. | 607/96 |
| 2010/0057173 A1 | | 3/2010 | Leavitt | |
| 2012/0316626 A1 | | 12/2012 | Dolivier et al. | 607/108 |
| 2013/0116760 A1 | | 5/2013 | Carson et al. | A61F 7/10 |
| 2014/0107739 A1 | * | 4/2014 | Kirkman | A61F 7/10 607/112 |
| 2014/0277301 A1 | | 9/2014 | Varga | |
| 2015/0224015 A1 | * | 8/2015 | Wilford | A61H 9/0078 601/151 |
| 2016/0051404 A1 | | 2/2016 | Choucair et al. | A61F 7/10 |

FOREIGN PATENT DOCUMENTS

| | | | |
|---|---|---|---|
| JP | H06178792 | 8/1994 | |
| JP | 2000217685 A | 8/2000 | |
| KR | 20040019830 | 3/2004 | A61F 7/02 |
| KR | 20130044897 | 3/2013 | |
| WO | 2015-0120368 | 8/2015 | A61H 39/06 |

OTHER PUBLICATIONS

International Search Report and Written Opinion issued in corresponding foreign application, PCT/US2018/025287, pp. 1-11 (dated Sep. 25, 2018).
First Office Action issued in corresponding foreign application, CN201880000941.1, pp. 1-10 (dated Dec. 2, 2019).
Extended European Search Report issued in corresponding foreign application, EP 17856940.6, pp. 1-7 (dated Apr. 21, 2020).
Second Office Action issued in corresponding foreign application, CN201880000941.1, pp. 1-11 (dated May 8, 2020).
Extended European Search Report issued in corresponding foreign application, EP 18778334.5, pp. 1-7 (dated Dec. 18, 2020).
Office action Issued by the JPO for application 2019-517240.

* cited by examiner

THERMAL PACK THAT CONFORMS TO CURVED SURFACES

BACKGROUND

The present invention relates thermal packs.

The invention more particularly relates to thermal packs that are designed to conform to anatomical structures.

Thermal packs are applied to anatomical forms and other curved surfaces for transferring thermal energy by way of a thermal material, such as a water, gel or clay, in the pack. It is desirable for a thermal pack to conform as closely as possible to an anatomical forms and other curved surfaces to which it is applied in order to achieve optimal energy transfer and comfort. Indeed, almost any thermal pack will conform closely to a flat surface or soft curve. However, anatomical forms such as the human body and other curved surfaces have bends and sharp curves as well.

Thermal packs comprising a single cell of material do not conform well to sharp curves because they have limited flexibility. A given such pack could be made more flexible by constructing it with less thermal material. But having less thermal material will mean that the desired functionality of the pack—to transfer heat to or from the body that it is applied to—will be compromised. In a limiting case, a single-cell pack could be made extremely flexible by providing only a very small amount of thermal material but then, of course, its intended functionality would be essentially lost altogether.

It is known that the flexibility and fit of thermal packs can be improved by combining a series of cells into a grid, with each cell containing a trapped body of thermal material. The pack can flex at the interface between adjoining cells and thus can more readily conform to body curves.

Another advantage of this approach is that, unlike a single cell pack, there is no opportunity for the thermal material to pool—i.e., aggregate in certain portions of the pack while leaving other portions with little or no thermal material—since the thermal material within a cell is trapped there within.

While an improvement over a single-cell design, multi-cell thermal packs as known in the art may still not able to conform well to certain anatomical features or other curved surfaces, such as those that are generally round and/or have particularly sharp curves. This issue has been addressed to some extent by multi-cell thermal packs that are customized for specific anatomical features or other curved surfaces. However, such customized thermal packs may not conform well to other anatomical features or other curved surfaces.

SUMMARY

A thermal pack embodying the principles of the present invention comprises first and second plastic sheets that form a sack. The sack contains a flowable thermal material and further includes a plurality of joint lines within the sack that are in contact with the thermal material.

The pack is able to conform to curved surfaces as would a single cell pack made of similar materials but the joint lines serve to keep the flowable material in place.

The joint lines may have any desired shape, e.g. straight, curved and/or undulating lines. Moreover, the joint lines may be arranged in any desired pattern. In particular embodiments, the joint lines are in arranged such that a pattern of tessellated shapes is formed.

In some embodiments the joint lines may be arranged in such a way as to create closed cells each containing a respective portion of the thermal material. The flowable material may, in some embodiments, be able to flow to some extent within its closed cell. However, because the flowable material is contained within the cells, even an acute bending of the pack around an acute body part, such as an elbow, for example, will still result in there being thermal material in close contact with the body part. This is in contrast to a single cell therapy pack with a flowable material since in such a pack there will be more of a tendency of the flowable material to be displaced away from the acute portion of the body.

In other embodiments there are gaps between various ones of the joint lines, which is to say that such embodiments do not have closed cells. A gap may equivalently be understood as being a perforation or discontinuity of a single joint line. The presence of the gaps means that the thermal material can flow within the pack through the gaps under the pressure of the pack being flexed. Indeed, the joint lines are arranged in such a way that the thermal material can flow in intersecting directions—colloquially "up and down," "left and right" and diagonally. This feature may allow the pack to flex to a greater extent than in embodiments where the joint lines are arranged in a way that creates closed cells. At the same time, the presence of the joint lines inhibits the thermal material within the pack from flowing so freely within the pack as to result in the thermal material pooling at the pack edges under pressure caused by the flexing and/or under the influence of gravity, as would tend to be the case of a pack with flowable thermal material that does not have joint lines, e.g. a single-cell pack. Indeed, to this end, it may be advantageous in particular embodiments for the joint lines and gaps to be arranged in such a way as to minimize or eliminate straight-line paths for the flow of thermal material through the gaps. A particular embodiment disclosed herein meeting this criterion is a pack in which the joint lines are arranged to form a pattern of tessellated hexagons with gaps in selected ones of the joint lines that constitute the hexagon edges.

DETAILED DESCRIPTION

Figure 1A:
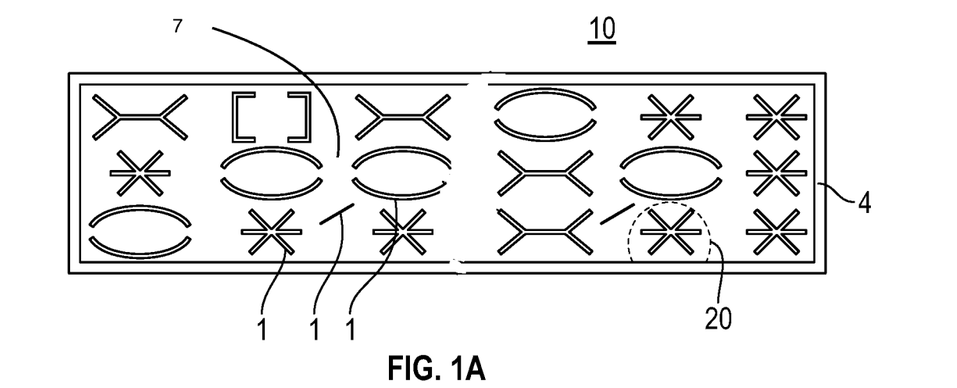
FIG. 1A is a plan view of an embodiment of the invention illustrating a variety of joint shapes and an arbitrary arrangement of joints.
Figure 1B:
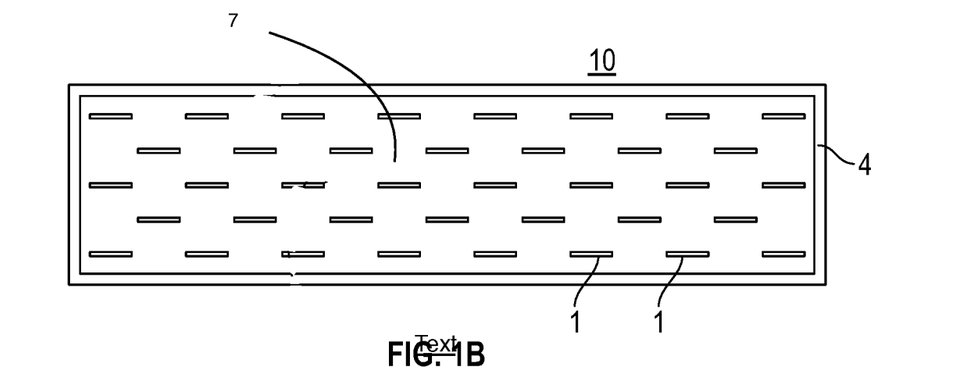
FIG. 1B is a plan view of an embodiment of the invention illustrating the joints arranged in parallel lines.
Figure 1C:
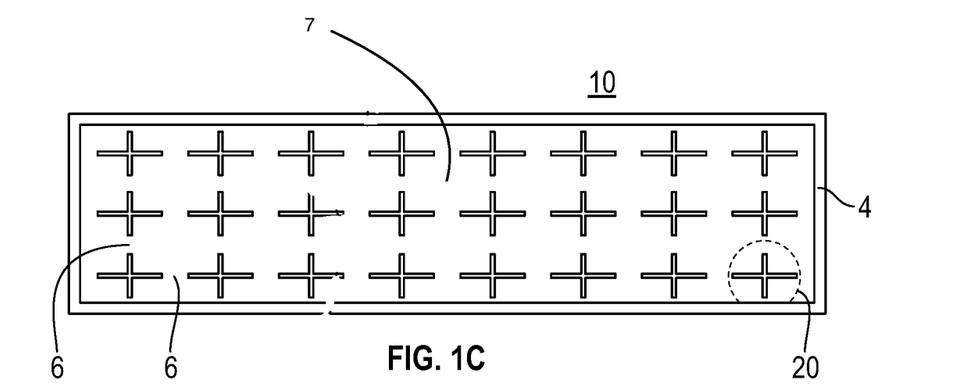
FIG. 1C is a plan view of an embodiment of the invention illustrating the joints arranged in crosses.
Figure 3A:
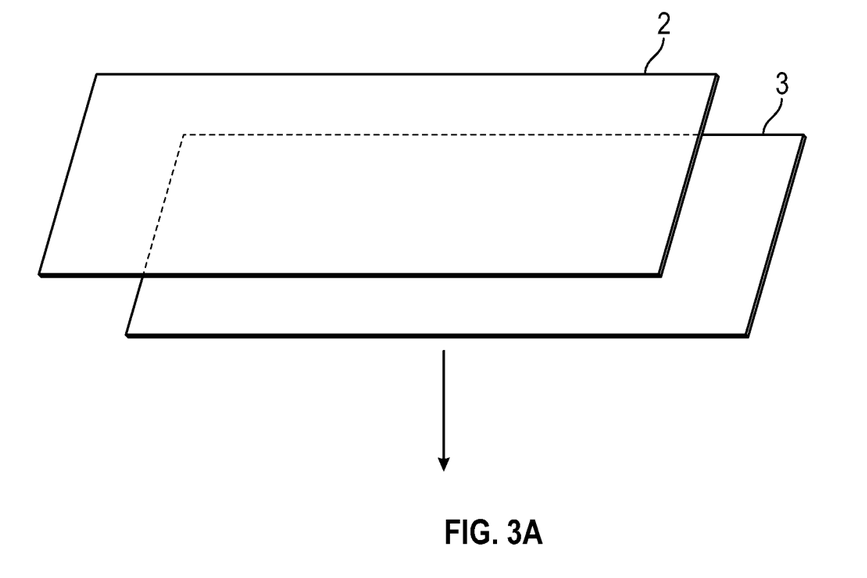
FIG. 3A is a simplified view of an embodiment of the invention illustrating first and second sheets of plastic that are joined together to form the thermal pack.
Figure 3B:
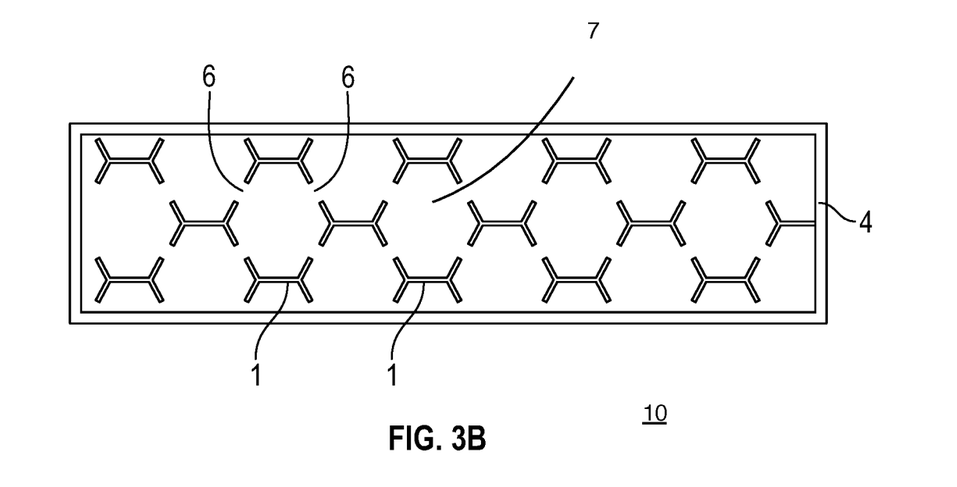
FIG. 3B is a plan view of an embodiment of the invention formed by joining the first and second sheets in FIG. 3A.

FIGS. 1A through 1C depict a pack 10, in accordance with the invention, for transferring heat to and from the body, comprising a plurality of joint lines 1 and a body of thermal material 7 within the pack. In this particular embodiment, the pack 10 comprises a soft-plastic top sheet 2 and soft-plastic bottom sheet 3 as shown in FIG. 3A. FIG. 3B depicts the two sheets 2 and 3 joined together at their perimeters 4 forming a sack with a fully enclosed interior and further joined to form the joint lines 1, which are in contact with the thermal material. In this view only top sheet 2 is visible. In practice, perimeters 4 and joint lines 1 may be formed by heat sealing the first sheet 2 and second sheet 3 together at the desired locations.

Figure 2A:
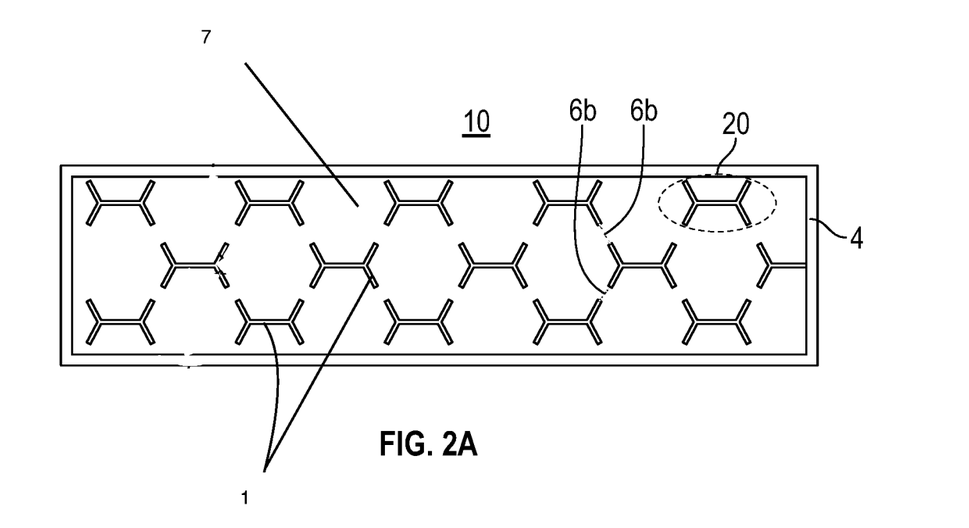
FIG. 2A is a plan view of an embodiment of the invention illustrating a pattern of joints forming a tessellated pattern of hexagons.
Figure 2B:
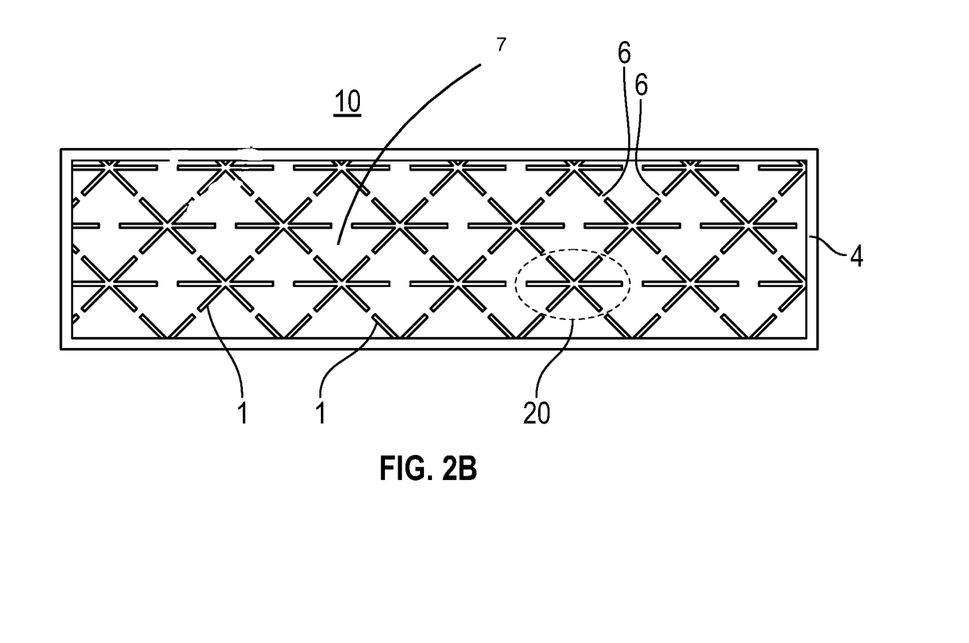
FIG. 2B is a plan view of an embodiment of the invention illustrating a pattern of joints forming a tessellated pattern of triangles.

As depicted in FIG. 1A, in a particular embodiment, the joint lines 1 may assume a variety of forms, e.g. straight, curved and/or undulating. The joint lines 1 may be grouped to form a variety of shapes and arranged in any desired pattern. A group 20 is illustrated in FIGS. 1A and 1C. Or the joint lines 1 may be joined such that the final form is not a collection of lines but a closed 2-dimensional shape. In this embodiment, the pack may to some extent flex along an edge or point of the group 20. As shown in FIG. 2A-2B, the groups 20 are tessellated across the pack 10. The tessellated groups 20 may assume a wide variety of shapes. As depicted in FIG. 2A, a particular embodiment features groups 20 tessellated in a hexagonal pattern. Given such a pattern, the pack 10 can flex out of the plane of the pack 10 at the hexagon vertices, allowing the pack 10 to take on an approximately spherical curve. Other possible arrangements of joint lines 1 may provide one or more of the advantages described herein but might to some extent inhibit flexing of the pack 10. As depicted in FIG. 2B, a particular embodiment features groups 20 tessellated in a triangle pattern. Such a pack 10 can flex out of the plane of the pack 10 at the triangle vertices, also allowing the pack 10 to take on an approximately spherical curve. The groups 20 may be arranged in a wide variety of repeating patterns, that are not necessarily tessellated.

Figure 4:
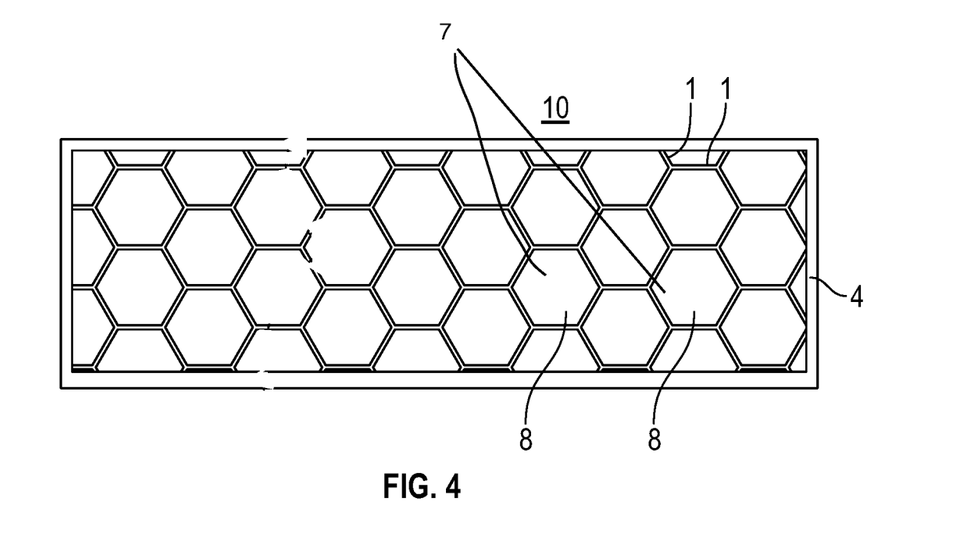
FIG. 4 is a plan view of the invention illustrating an embodiment with closed cells.
Figure 5:
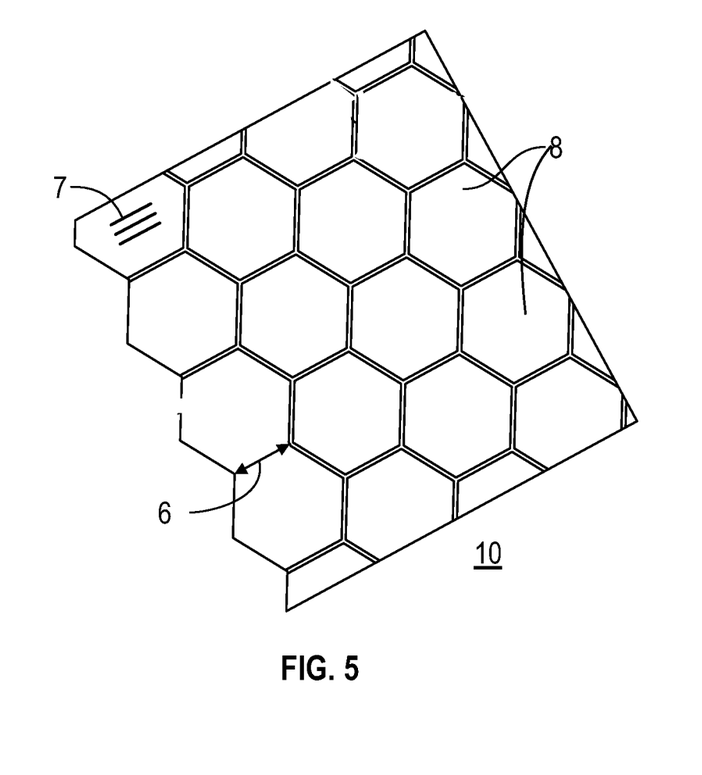
FIG. 5 is a perspective view of a cross-section of the embodiment of FIG. 4.

As depicted in FIG. 4, the joints 1 in a particular embodiment may be arranged in such a way as to create closed cells 8 each containing a respective portion of a thermal material 7 (the thermal material is shown in FIG. 5). The closed cells 8 are arranged in a pattern of tessellated hexagons. However, the closed cells 8 may be in other repeating patterns, e.g., tessellated or otherwise. As depicted in FIG. 2A, in a particular embodiment, there are gaps 6 between the various joint lines 1. A gap 6 may equivalently be understood as being a perforation or discontinuity of a single joint line 1. The presence of the gaps 6 means that in embodiments in which the thermal material 7 is a flowable material, such as a gel, the thermal material 7 can flow within the pack 10 through the gaps 6 under the pressure of the pack 10 being flexed. This may allow the pack 10 to flex to a greater extent than in embodiments where the joint lines 1 are arranged in a way that create closed cells 8.

In a particular embodiment, the thermal material 7 is a bentonite and glycol blend which can be heated above body temperature for transferring heat to the body and chilled for absorbing heat from the body. This mixture will not freeze solid when cooled at normal freezer temperatures of approximately zero degrees Fahrenheit. A pack 10 with this type of thermal material 7 further allows the pack 10 to conform to the body. In a particular embodiment, the thermal material has a heat capacity greater than 0.4. In a particular embodiment, the thermal material has a higher viscosity than water. In a particular embodiment, the thermal material, has a higher viscosity than 50,000 centipoise. In a particular embodiment, the thermal material has a viscosity higher than 150,000 centipoise.

The presence of the joint lines 1 inhibit the thermal material 7 within the pack from flowing so freely within the pack as to result in the thermal material 7 pooling at the pack 10 edges under pressure caused by the flexing and/or under the influence of gravity, as would tend to be the case of a pack 10 with flowable thermal material 7 that does not have joint lines 1, e.g. a single-cell pack. As such, it may be advantageous for the joint lines 1 and gaps 6 to be arranged in such a way as to minimize or eliminate straight-line paths for the flow of thermal material 7 through the gaps 6. As depicted in FIG. 2A, for example, a pack 10 meeting this criterion has joint lines 1 arranged to form a pattern of tessellated hexagons with gaps 6 and joint lines 1 constituting the hexagon edges. A pattern may be formed by any desired cell shapes and/or arrangement of joint shapes 20 and/or joint lines 1.

In practice, the pack 10 may be of any suitable material and, in particular embodiments the sheets are of plastic. One possibility is a polymer, such as polyethylene, polyester, polypropylene, nylon, poly-vinyl chloride, and combinations of these materials, as well as laminates of multiple materials. Pack 10 may be free of latex and other allergenic materials. The pack 10 may also be textured on its exterior for comfortable contact with skin of the body.

Figure 6:
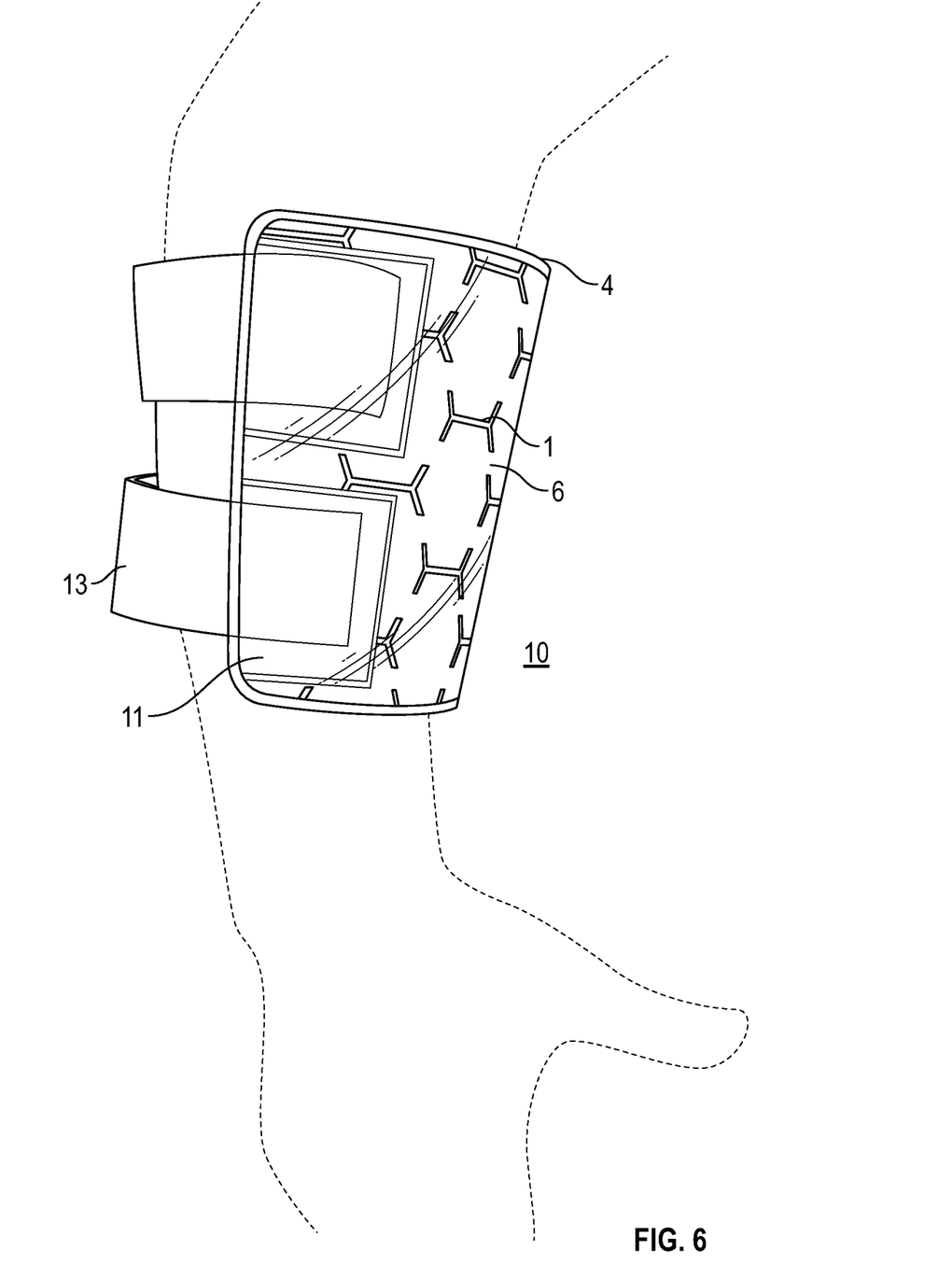
FIG. 6 is a perspective view of an embodiment of the invention as applied to a forearm.
Figure 7:
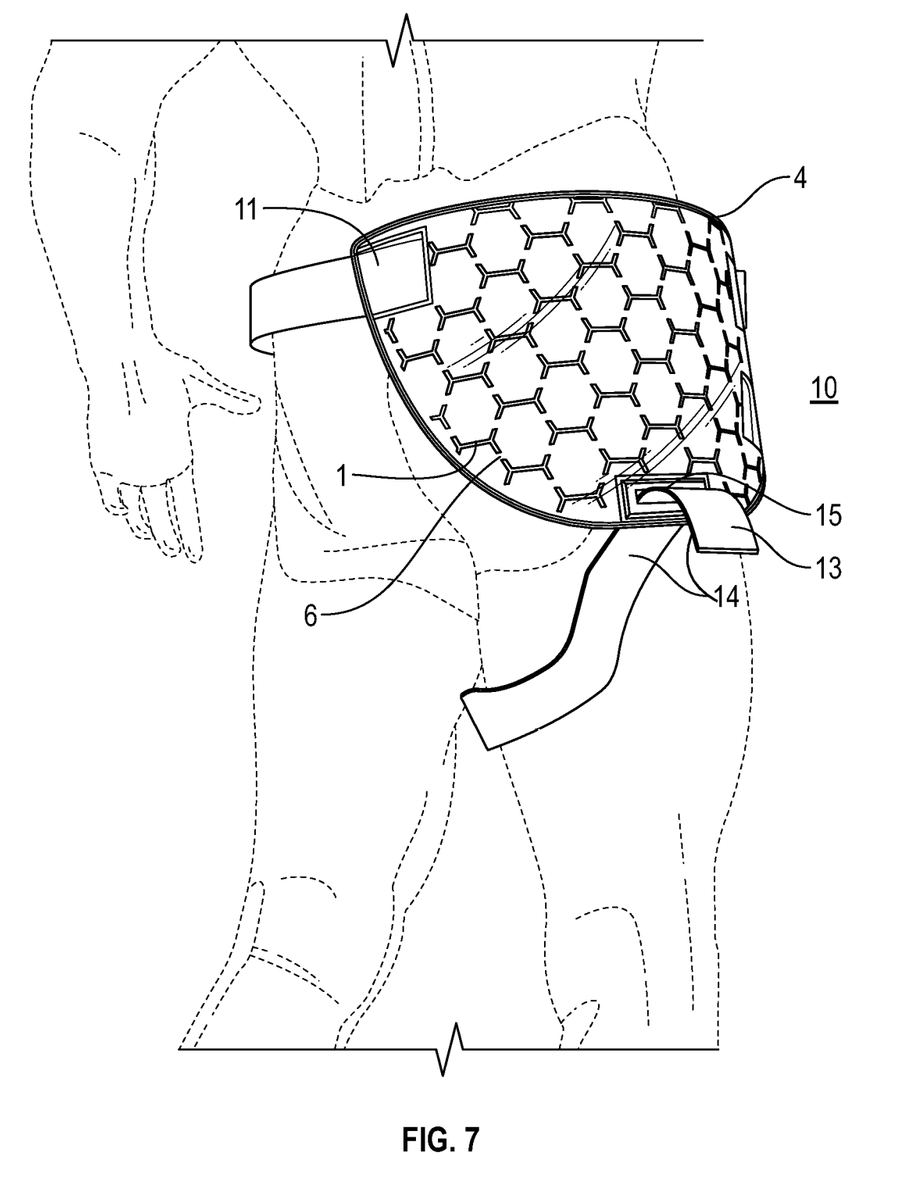
FIG. 7 is a perspective view of an embodiment of the invention as applied to a hip.

As depicted in FIGS. 6-7, an embodiment of the pack 10 comprises one or more straps 13 mounted to the pack 10 at a strap mount 11. However, the thermal pack 10 may be secured to an anatomical structure in a variety of ways with or without any of a variety of fasteners. For example, a person may hold the thermal pack against a portion of the body. The present inventor has found the thermal pack 10 is advantageously secured to the body with straps 13 mounted to the pack having a hook and loop system 14, as shown in FIG. 7. The straps 13 are mounted to the pack 10 by being fastened to or through one or more apertures 15 formed in the pack 10 and fastened back on itself with a hook and loop system 14.

Figure 8:
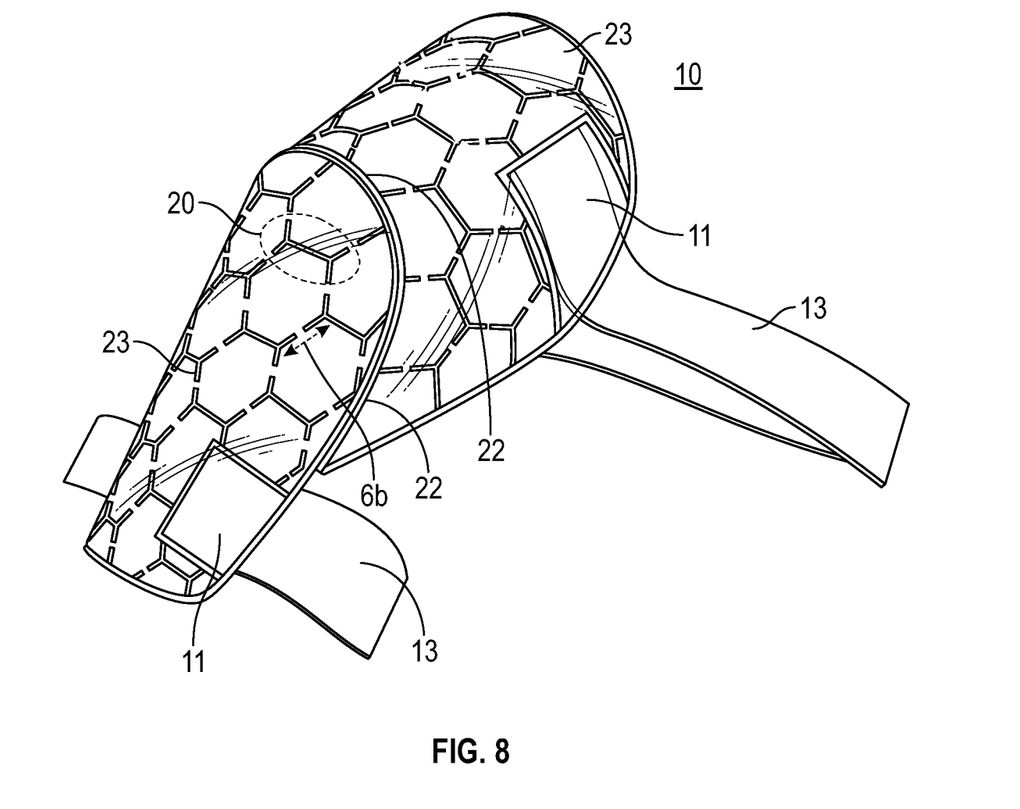
FIG. 8 is a perspective view of an embodiment of the invention shaped for application to a shoulder.
Figure 9:
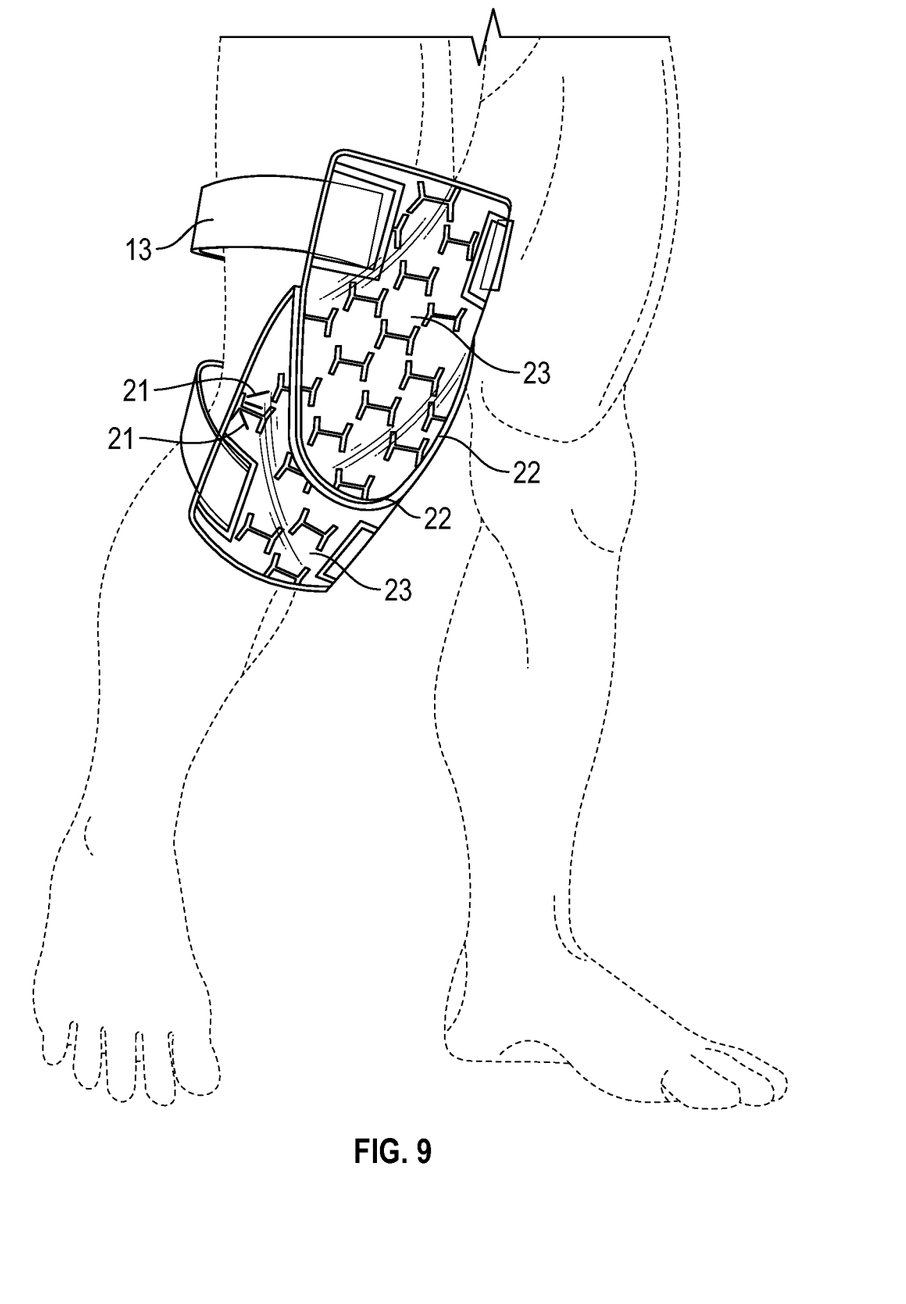
FIG. 9 is a perspective view of an embodiment of the invention as applied to a knee.

As depicted in FIGS. 8-9 in a particular embodiment multiple packs 10 may be joined to form-fit an anatomical structure. As the curve of an anatomical structure sharpens, it often forms a partial-sphere like structure, such as a bent knee or at the shoulder arm interface. The multiple-pack assembly may be form-fitted by notching, patterning, and joining multiple packs 10 together. As depicted in FIG. 9, the pack 10 has notches 21, where a portion of one of the packs 10 is removed and the resulting adjacent edges of the pack 10 are joined together. The edges of the notches 21 may be joined by heat-fusing the two edges together. The benefit of notching is to shape the pack 10 around a spherical or other rounded structure, e.g., a bent knee. Patterning is achieved when the pack 10 is formed into a shape, such as shaped portions 23, as depicted in FIG. 8 and FIG. 9. The shaped portions 23 may be joined together to form a more complex shape, e.g., the embodiment shown in FIG. 8 is shaped to fit a shoulder and FIG. 9 is shaped to fit a knee. The packs may be formed to fit a wide variety of anatomical structures with these methods for joining packs 10.

The foregoing merely illustrates the principles of the invention. It will be appreciated that those skilled in the art will be able to devise numerous alternative arrangements that while not shown or described herein, embody the principles of the invention and thus are within its spirit and scope.

What is claimed is:

1. A thermal pack comprising:
a first flexible sheet and a second flexible sheet joined together forming a sack, the sack comprising a sack perimeter, a sack outer surface, a sack inner plenum bound by the first flexible sheet and the second flexible sheet along the sack perimeter, and a flowable thermal material enclosed in the sack inner plenum;
a plurality of joint lines joining portions of the first flexible sheet and the second flexible sheet within the sack inner plenum forming a plurality of hexagonal shaped thermal material cells, each thermal material cell of the plurality of hexagonal shaped thermal material cells sharing a joint line as a hexagonal thermal material cell perimeter boundary line with an adjacent thermal material cell thereby forming a tessellated pattern;
the hexagonal shaped thermal material cells having six faces wherein a first face joins a second face forming a first obtuse angle section, the second face joins a third face forming a second obtuse angled section, the third face joins a fourth face forming a third obtuse angled section, the fourth face joins a fifth face forming a fourth obtuse angled section, the fifth face joins the a sixth face forming a fifth obtuse angled section, the sixth face joins the first face forming a sixth obtuse angled section;
the hexagonal shaped thermal material cells further having a first gap disposed in the first face, a second gap is disposed in the second face, a third gap is disposed in the fourth face, and a fourth gap is disposed in the fifth face;
the hexagonal shaped thermal material cells having an upper thermal material retaining portion comprising the first obtuse angled section, the second face, and the second obtuse angled section configured to deflect thermal material flow towards a hexagonal shaped thermal material cell center;
the hexagonal shaped thermal material cells further having a first lateral thermal material retaining portion comprising the sixth obtuse angled section and a second lateral thermal material retaining portion comprising the third obtuse angled section, the first and second lateral thermal material retaining portions configured to deflect thermal material flow towards the hexagonal shaped thermal material cell center; and
the hexagonal shaped thermal material cells having an lower thermal material retaining portion comprising the fourth obtuse angled section, the fifth face, and the fifth obtuse angled section configured to retain thermal material flowing into the hexagonal shaped thermal material cell and deflect excess thermal material flow towards the hexagonal shaped thermal material cell center.

2. The thermal pack of claim 1, wherein the thermal pack has at least one V-shaped notch and adjacent edges of the at least one V-shaped notch are joined together to form-fit or shape the thermal pack around a spherical or rounded structure.

3. The thermal pack of claim 1 wherein the tessellated pattern is configured to allow the thermal pack to form a spherical curve along the joint lines conforming all sack surfaces parallel to a spherical curved surface upon flexing at the plurality of joint lines.

4. The thermal pack of claim 1 wherein the flowable thermal material comprises bentonite and glycol or water.

5. The thermal pack of claim 1 wherein the flowable thermal material comprises a heat capacity greater than 0.4.

6. The thermal pack of claim 1 wherein the flowable thermal material comprises a viscosity higher than water.

7. The thermal pack of claim 1 wherein the flowable thermal material comprises a viscosity higher than 50,000 centipoise.

8. The thermal pack of claim 1 wherein the flowable thermal material comprises a viscosity higher than 150,000 centipoise.

9. The thermal pack of claim 1 comprising at least a second sack, non-removably bonded to the sack along a perimeter curve of each the sack and the at least second sack forming a seam following a three-dimensional trajectory such that the bonded sacks form a sack interior surface in a shape of a three-dimensional surface.

10. A thermal pack comprising:
a first flexible sheet and a second flexible sheet joined together forming a sack, the sack comprising a sack perimeter, a sack outer surface, a sack inner plenum bound by the first flexible sheet and the second flexible sheet along the sack perimeter, and a flowable thermal material enclosed in the sack inner plenum;
a plurality of joint lines joining portions of the first flexible sheet and the second flexible sheet within the sack inner plenum forming a plurality of triangular shaped thermal material cells, each thermal material cell of the plurality of triangular shaped thermal material cells sharing a joint line as a thermal material cell perimeter boundary line with an adjacent thermal material cell thereby forming a tessellated pattern;
the triangular shaped thermal material cells having three faces wherein a first face joins a second face forming a first angled section, the second face joins a third face forming a second angled section, the third face joins the first face forming a third angled section;
the triangular shaped thermal material cells further having a first gap disposed in the first face, a second gap is disposed in the second face, a third gap is disposed in the third face;
the triangular shaped thermal material cells having an upper thermal material retaining portion comprising the first angled section, configured to deflect thermal material flow towards a triangular shaped thermal material cell center;
the triangular shaped thermal material cells further having a first lower thermal material retaining portion comprising the third angled section and a second lower thermal material retaining portion comprising the second angled section, the first and second lower thermal material retaining portions configured to deflect thermal material flow towards the triangular shaped thermal material cell center.

11. The thermal pack of claim 10, wherein the thermal pack has at least one V-shaped notch and adjacent edges of the at least one V-shaped notch are joined together to form-fit or shape the thermal pack around a spherical or rounded structure.

12. The thermal pack of claim 10 wherein the tessellated pattern is configured to allow the thermal pack to form a spherical curve upon flexing at the plurality of joint lines.

13. The thermal pack of claim 10 wherein the tessellated pattern is formed of triangular shaped thermal material cells flexing out of the surface plane at triangular vertices of the triangular shaped thermal material cells.

14. The thermal pack of claim 10 wherein the flowable thermal material comprises bentonite and glycol or water.

15. The thermal pack of claim 10 wherein the flowable thermal material comprises a heat capacity greater than 0.4.

16. The thermal pack of claim 10 wherein the flowable thermal material comprises a viscosity higher than water.

17. The thermal pack of claim 10 wherein the flowable thermal material comprises a viscosity higher than 50,000 centipoise.

18. The thermal pack of claim 10 wherein the flowable thermal material comprises a viscosity higher than 150,000 centipoise.

19. The thermal pack of claim 10 comprising at least a second sack, non-removably bonded to the sack along a perimeter curve of each the sack and the at least second sack forming a seam following a three-dimensional trajectory such that bonded sacks form a sack interior surface in a shape of a three-dimensional surface.

* * * * *